(12) United States Patent
Beumer et al.

(10) Patent No.: US 9,434,676 B2
(45) Date of Patent: Sep. 6, 2016

(54) FLAVOR AND FRAGRANCE FORMULATION (VI)

(71) Applicant: DSM IP ASSETS B.V., Heerlen (NL)

(72) Inventors: Raphael Beumer, Basel (CH);
Johannes Tschumi, Basel (CH);
Michael Gressly, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/432,252

(22) PCT Filed: Oct. 7, 2013

(86) PCT No.: PCT/EP2013/070838
§ 371 (c)(1),
(2) Date: Mar. 30, 2015

(87) PCT Pub. No.: WO2014/056853
PCT Pub. Date: Apr. 17, 2014

(65) Prior Publication Data
US 2015/0291505 A1    Oct. 15, 2015

(30) Foreign Application Priority Data
Oct. 8, 2012   (EP) .................................. 12187652

(51) Int. Cl.
| | | |
|---|---|---|
| *A61K 8/18* | (2006.01) | |
| *A61Q 13/00* | (2006.01) | |
| *C07C 69/145* | (2006.01) | |
| *C11B 9/00* | (2006.01) | |
| *C11D 3/50* | (2006.01) | |
| *A23L 1/226* | (2006.01) | |
| *A61K 8/34* | (2006.01) | |
| *A61K 8/37* | (2006.01) | |
| *C07C 33/025* | (2006.01) | |
| *C07C 67/00* | (2006.01) | |

(52) U.S. Cl.
CPC .......... *C07C 69/145* (2013.01); *A23L 1/22635* (2013.01); *A23L 1/22642* (2013.01); *A61K 8/342* (2013.01); *A61K 8/37* (2013.01); *A61Q 13/00* (2013.01); *C07C 33/025* (2013.01); *C07C 67/00* (2013.01); *C11B 9/0015* (2013.01); *C11B 9/0019* (2013.01); *C11D 3/50* (2013.01)

(58) Field of Classification Search
CPC ... C07C 69/145; C07C 67/00; C07C 33/025; C11B 9/0019; C11B 9/0015; A63L 1/22635; A63L 1/22642; C11D 3/50; A61K 8/37; A61K 8/342; A61Q 13/00
USPC .................................................. 512/26, 25, 1
See application file for complete search history.

(56) References Cited

U.S. PATENT DOCUMENTS 4,524,783 A    6/1985   Wiegers et al.

FOREIGN PATENT DOCUMENTS

| | | |
|---|---|---|
| DE | 905 189 | 2/1954 |
| EP | 1 837 326 | 9/2007 |
| GB | 1 227 400 | 4/1971 |

OTHER PUBLICATIONS

Naves et al., "Volumen Analytisches Laboratorium der", Helvetica Chimica Acta, vol. 30, No. 6, Jan. 1, 1947, pp. 2551-2558.*
International Search Report for PCT/EP2013/070838 mailed Feb. 7, 2014, 4 pages.
Naves et al., "Volumen Analytisches Laboratorium der", Helvetica Chimica Acta, vol. 30, No. 6, Jan. 1, 1947, pp. 1599-1613.
International Preliminary Report on Patentability, PCT/EP2013/070838 (Apr. 16, 2015).

* cited by examiner

*Primary Examiner* — Ling Choi
*Assistant Examiner* — Jessica E Whiteley
(74) *Attorney, Agent, or Firm* — Nixon & Vanderhye P.C.

(57) ABSTRACT

The present invention relates to the use of specific organic compounds of formula (I) as flavor and fragrance material. Furthermore the invention relates to a new specific organic compound, as well as to flavor and fragrance formulations comprising at least one of the specific organic compounds.

7 Claims, No Drawings

FLAVOR AND FRAGRANCE FORMULATION (VI)

This application is the U.S. national phase of International Application No. PCT/EP2013/070838, filed 7 Oct. 2013, which designated the U.S. and claims priority to EP Patent Application No. 12187652.8, filed 8 Oct. 2012, the entire contents of each of which are hereby incorporated by reference.

The present invention relates to the use of specific organic compounds as flavor and fragrance material. Furthermore the invention relates to new specific organic compounds, as well as to flavor and fragrance formulations comprising at least one of the specific organic compounds.

In the flavor and fragrance industry there is always a need and demand for compounds that enhance, modify, improve or otherwise positively influence an odor note and therefore give perfumers or other persons the ability to create new fragrances for perfumes, colognes, personal care products, household products or any other products, which comprise flavor and fragrance materials.

Surprisingly it was found that the compounds of formula (I) are very useful as flavor and fragrance material.

Therefore the present invention is related to the use of a compound of formula (I)

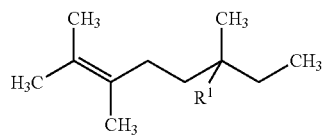

wherein $R^1$ signifies —OH (hydroxy) or —O(CO)CH$_3$ (acetyloxy; "OAc"), as flavor and fragrance material.

Preferred is the use of at least one compound selected from the group consisting of the compounds of formulae (Ia) and (Ib) as well as any mixture thereof

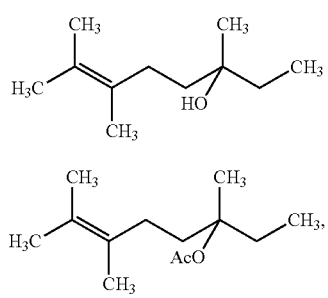

as flavor and fragrance material, whereby the use of the compound of formula (Ib) is especially preferred.

The compounds of formula (I) may be used as such or in combination with other compounds of formula (I) or other compounds which are known as flavor and fragrance material.

Such other compounds which are known as flavor and fragrance material include all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in flavor fragrance formulations, for example, carrier materials, and other auxiliary agents commonly used in the art.

The flavor and fragrance material of the present invention is used in a flavor and fragrance formulation.

Such a flavor and fragrance formulation comprises other ingredients.

The flavor and fragrance formulation according to the present invention can be in any form. Usually it is in a solid, gel-like or liquid (or a combination thereof) form.

It can also be in an encapsulated form (i.e. a liquid formulation encapsulated by a suitable matrix material).

Therefore the present invention also relates to flavor and fragrance formulations comprising (i) at least one compound of formula (I)

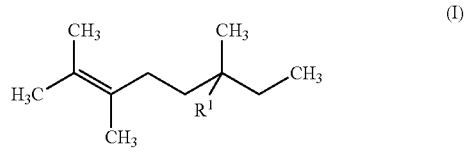

wherein $R^1$ is —OH or —O(CO)CH$_3$, preferably wherein $R^1$ is —O(CO)CH$_3$.

Preferred are flavor and fragrance formulations comprising at least one compound selected from the group consisting of the compounds of formulae (Ia) and (Ib) as well as any mixture thereof

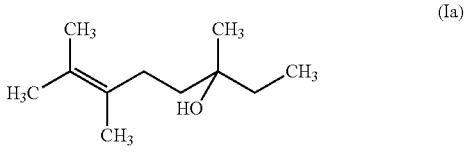

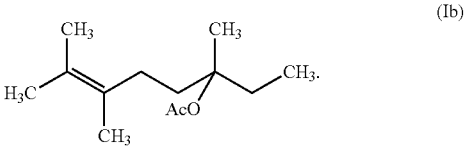

When a compound of formula (I) is used in a flavor and fragrance formulation, then the amount thereof is in the range of 0.0001-10 weight-% (wt-%), related to the total weight of the flavor and fragrance formulation. Preferred is an amount in the range of 0.01-5 wt-%.

Therefore the present invention relates to liquid flavor and fragrance formulations comprising (i) 0.0001-10 wt-% (preferably 0.01-5 wt-%), related to the total weight of the flavor and fragrance formulation of at least one compound of formula (I).

The flavor and fragrance formulations according to the present invention can comprise further ingredients (=auxiliary compounds), such as any further perfuming compounds solvents, adjuvants, thickeners, surface active agents, pigments, extenders, rheology modifiers, dyestuffs, antioxidants, fillers and the like.

Many flavor and fragrance formulations are in a liquid form (like a perfume, cologne, etc.). Therefore, for such liquid formulation a (diluent) solvent is present. Such common diluents are i.e. dipropyleneglycol, isopropylmyristate, triethylcitrate and alcohols (such as ethanol).

Further examples of fine perfumery are Eau de perfume, Eau de Toilette, Eau de Cologne and Splash Cologne. Fine perfumery products are commonly based on an alcoholic solution as diluent. However fine perfumery products using an oil or wax as diluent are also included within the meaning of the present invention. The compounds can be employed in widely varying amounts, depending upon the specific application and on the nature and quantity of other odorant ingredients.

When used in a (fine) perfume, the amount is usually between 0.01-10 wt-%, based on the total weight of the (fine) perfume.

However, these values and ranges are given only by way of example, since the experienced perfumer may also achieve effects or may create novel accords with lower or higher concentrations.

Furthermore the present invention relates to liquid flavor and fragrance formulations comprising
(i) at least one compound of formula (I) with the preferences as given above, and
(ii) at least one diluent chosen from the group consisting of dipropyleneglycol, isopropylmyristate, triethylcitrate and alcohols (such as ethanol), and optionally
(iii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to solid flavor and fragrance formulations comprising
(i) at least one compound of formula (I) with the preferences as given above and
(ii) at least one auxiliary compound selected from the group consisting of perfuming compounds solvents, adjuvants, thickeners, surface active agents, pigments, extenders, rheology modifiers, dyestuffs, antioxidants and fillers.

The compounds of formula (I) with the preferences as given above may be used in a broad range of flavor and fragrance formulations, e.g. in any field of fine and functional perfumery, such as perfumes, air care products, household products, laundry products, body care products and cosmetics.

The compounds as described hereinabove may be employed in a flavor and fragrance formulation simply by directly mixing at least one compound of formula (I) with the preferences as given above, a mixture thereof, or a fragrance composition with the other ingredients used in the final product, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the other ingredients used in the final product.

Thus, the invention additionally provides a method of manufacturing a flavor and fragrance formulation, comprising the incorporation of a compound of formula (I) with the preferences as given above, as a fragrance ingredient, either by directly admixing the compound to the other ingredients used in the final product or by admixing a fragrance composition comprising a compound of formula (I) with the preferences as given above, which may then be mixed with the other ingredients used in the final product, using conventional techniques and methods.

Through the addition of an olfactory acceptable amount of a compound of the present invention as hereinabove described, or a mixture thereof, the odor notes of a consumer product base will be improved, enhanced or modified.

Thus, the invention furthermore provides a method for improving, enhancing or modifying a consumer product (=final product) base by means of the addition thereto of an olfactorily acceptable amount of a compound of formula (I) with the preferences as given above, or a mixture thereof.

In the context of the present invention the olfactory effective amount is to be understood as the amount of the at least one compound of formula (I) with the preferences as given above in a flavor and fragrance formulation will contribute to its particular olfactory characteristics, but the olfactory effect of the flavor and fragrance formulation will be the sum of the effects of each of the perfumes or fragrance ingredients. Thus the compounds of the invention can be used to alter the aroma characteristics of the flavor and fragrance formulation, or by modifying the olfactory reaction contributed by another ingredient in the composition. The amount will vary depending on many factors including other ingredients, their relative amounts and the effect that is desired.

As used herein, "consumer product (=final product)" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body care products, e.g. shampoo, shower gel; air care products and cosmetics, e.g. deodorant, vanishing creme. This list of products is given by way of illustration and is not to be regarded as being in any way limiting.

The compounds of formula (I) may be prepared using methods known to the person skilled in the art of organic synthesis.

Furthermore the present invention relates to the following compound of formula (Ib) which is a novel compound:

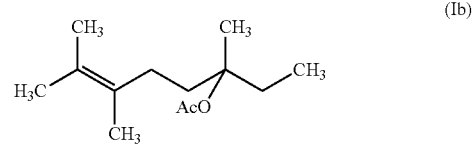

(Ib)

As stated above this compound is produced (manufactured, synthesized) using well known chemical reactions.

A preferred process for the manufacture of compound (Ib) starts from 5,6-dimethyl-5-hepten-2-on which is ethinylated to 3,6,7-Trimethyl-6-octen-1-in-3-ol which is then acylated to 3,6,7-Trimethyl-6-octen-1-in-3-yl acetate. The subsequent hydrogenation of the C≡C triple bond to the saturated C—C bond in the presence of a Lindlar catalyst then leads to the compound of formula (Ib). This process is also part of the present invention.

The invention is now further illustrated in the following non-limiting examples.

EXAMPLES

All compounds were evaluated by a panel of four persons for their intensity whereby a range of 1 to 10 was used (1=very low intensity; 10=very high intensity). Furthermore these four persons also described the odor of the compounds. The tenancy was evaluated by one person after 3, 6, 8, 24, 48, 72 and 96 hours. For such evaluations a piece of paper was immersed in each single liquid compound as such.

Example 1

Manufacture and Olfactory Properties of the Compound of Formula Ia 3,6,7-Trimethyl-6-octen-1-in-3-ol may be prepared by ethinylation of 5,6-dimethyl-5-hepten-2-on.

a) Manufacture of the Compound of Formula (Ia) by Hydrogenation of 3,6,7-trimethyl-6-octen-1-in-3-ol 383.0 g of 3,6,7-trimethyl-6-octen-1-in-3-ol and 0.3 g of Lindlar catalyst (5% Pd+3.5% Pb on CaCO₃) are put in an autoclave and heated under nitrogen to a temperature of 45° C. Nitrogen is exchanged by hydrogen (H₂) and the reaction mixture put at an absolute pressure of 2 bar. After the calculated amount of hydrogen has been consumed the reaction mixture is filtered and distilled (2 mbar, 115° C.) to obtain 3,6,7-trimethyl-6-octen-3-ol (=compound of formula (Ia)).

b) Odour Description plant; hop; wood; leek/field garlic; inside of rubber gloves; sweetish; sourish.
Intensity: 5.
Tenancy: 8-24 hours.

Example 2

Manufacture and Olfactory Properties of the Compound of Formula Ib 3,6,7-Trimethyl-6-octen-1-in-3-ol may be prepared by ethinylation of 5,6-dimethyl-5-hepten-2-on.

a) Manufacture of 3,6,7-trimethyl-6-octen-1-in-3-yl Acetate by Acylation of 3,6,7-trimethyl-6-octen-1-in-3-ol 650.0 g of 3,6,7-trimethyl-6-octen-1-in-3-ol and 0.63 g of p-toluene sulfonic acid in water are mixed and heated up to a temperature of 40° C. 479.3 g of acetic acid anhydride are added within 2 hours. After ca. 20 hours the reaction mixture is cooled down and distilled to obtain 3,6,7-trimethyl-6-octen-1-in-3-yl acetate.

b) Manufacture of the Compound of Formula (Ib) by Hydrogenation of 3,6,7-trimethyl-6-octen-1-in-3-yl Acetate 409.0 g of 3,6,7-trimethyl-6-octen-1-in-3-yl acetate and 20.0 g of Lindlar catalyst (5% Pd+3.5% Pb on CaCO₃) are put in an autoclave and heated under nitrogen to a temperature of 45° C. Nitrogen is exchanged by hydrogen (H₂) and the reaction mixture put at an absolute pressure of 2 bar. After the calculated amount of hydrogen has been consumed the reaction mixture is filtered and distilled (2 mbar, 130° C.) to obtain 3,6,7-trimethyl-6-octen-3-yl acetate (=compound of formula (Ib)).

c) Odour Description balsamic; creamy; dry stored wood; dry leaves.
Intensity: 4.
Tenancy: 6-8 hours.

The invention claimed is:

1. A flavor and fragrance formulation comprising at least one compound of formula (I):

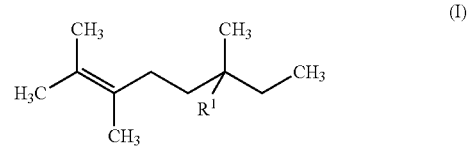

wherein R¹ is —OH or —O(CO)CH₃.

2. The flavor and fragrance formulation according to claim 1 comprising 0.0001-10 wt-%, relative to the total weight of the flavor and fragrance formulation, of at least one compound of formula (I).

3. The flavor and fragrance formulation according to claim 1, wherein the flavor and fragrance formulation is solid, gel-like or liquid.

4. The flavor and fragrance formulation according to claim 1, wherein the flavor and fragrance formulation is a perfume, hair care product, household product, laundry product, body care product or cosmetic product.

5. A method of improving, enhancing or modifying a flavor and fragrance formulation which comprises adding to the flavor or fragrance formulation an olfactory acceptable amount of at least one compound of formula (I):

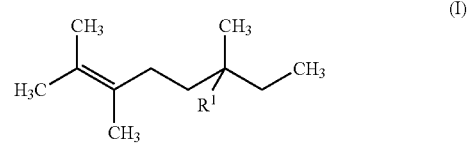

wherein R¹ is —OH or —O(CO)CH₃.

6. A compound of formula (Ib):

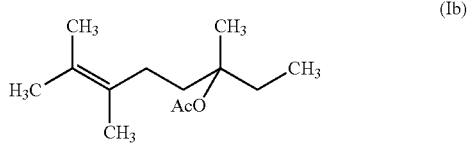

wherein AcO represents an acetyloxy group CH₃(CO)O—.

7. A process for the manufacture of a compound of formula (Ib):

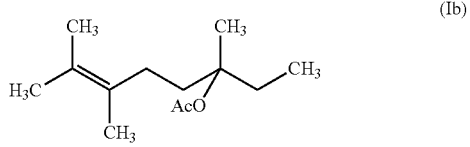

wherein AcO represents an acetyloxy group $CH_3(CO)O-$, the process comprising the steps of:
i) ethinylating 5,6-dimethyl-5-hepten-2-on to 3,6,7-trimethyl-6-octen-1-in-3-ol;
ii) acylating 3,6,7-trimethyl-6-octen-1-in-3-ol to 3,6,7-trimethyl-6-octen-1-in-3-yl acetate; and
iii) hydrogenating the C≡C triple bond of 3,6,7-trimethyl-6-octen-1-in-3-yl acetate to the saturated C—C bond in the presence of a Lindlar catalyst leading to the compound of formula (Ib).

* * * * *